United States Patent
Petermann

(10) Patent No.: US 10,513,599 B2
(45) Date of Patent: Dec. 24, 2019

(54) CELLULOSE ETHER ACETATE PHTHALATES

(71) Applicant: Dow Global Technologies LLC, Wilmington, DE (US)

(72) Inventor: Oliver Petermann, Hamburg (DE)

(73) Assignee: Global Dow Technologies LLC

( * ) Notice: Subject to any disclaimer, the term of this patent is extended or adjusted under 35 U.S.C. 154(b) by 0 days.

(21) Appl. No.: 16/072,691

(22) PCT Filed: Aug. 22, 2017

(86) PCT No.: PCT/US2017/047997
§ 371 (c)(1),
(2) Date: Jul. 25, 2018

(87) PCT Pub. No.: WO2018/039220
PCT Pub. Date: Mar. 1, 2018

(65) Prior Publication Data
US 2019/0177514 A1    Jun. 13, 2019

Related U.S. Application Data

(60) Provisional application No. 62/378,246, filed on Aug. 23, 2016.

(51) Int. Cl.
*C08L 1/32*     (2006.01)
*A61K 9/48*     (2006.01)

(52) U.S. Cl.
CPC .............. *C08L 1/32* (2013.01); *A61K 9/4816* (2013.01); *A61K 9/4833* (2013.01)

(58) Field of Classification Search
None
See application file for complete search history.

(56) References Cited

U.S. PATENT DOCUMENTS

| | | |
|---|---|---|
| 2014/0171441 A1 | 6/2014 | Babcock et al. |
| 2015/0374831 A1 | 12/2015 | Brackhagen et al. |

FOREIGN PATENT DOCUMENTS

| | | |
|---|---|---|
| WO | 2006082518 | 8/2006 |
| WO | 2014031448 | 2/2014 |
| WO | 2014137777 | 9/2014 |
| WO | 2015179073 | 11/2015 |

OTHER PUBLICATIONS

Kokubo et al., Development of Cellulose Derivatives as Novel Enteric Coating Agents Soluble at pH 3.5-45. and Higher, Chem. Pharm. Bull., 1997, 45, 8, pp. 1350-1353.

*Primary Examiner* — Bong-Sook Baek

(57) ABSTRACT

A cellulose ether acetate phthalate is provided, wherein the degree of substitution of phthalyl groups is from 0.02 to 0.25, the degree of neutralization of phthalyl groups is not more than 0.5, the degree of substitution of acetyl groups is from 0.02 to 0.40, and the total degree of substitution of phthalyl and acetyl groups is not more than 0.50. The cellulose ether acetate phthalate has a solubility in water of at least 2.0 weight percent at 2° C.

15 Claims, No Drawings

CELLULOSE ETHER ACETATE PHTHALATES

FIELD

This invention concerns novel cellulose ether acetate phthalates and their use for producing capsule shells or solid drug dispersions or for coating dosage forms.

INTRODUCTION

Various esterified cellulose ethers are useful in the pharmaceutical field, such as hydroxypropyl methyl cellulose phthalate (HPMCP), hydroxypropyl methyl cellulose acetate phthalate (HPMCAP) or hydroxypropyl methyl cellulose acetate succinate (HPMCAS). International Patent Application WO 2014/137777 discloses such esterified cellulose ethers of low viscosity in aqueous NaOH or acetone.

Some esterified cellulose ethers are known as enteric polymers for pharmaceutical dosage forms. Enteric polymers are those that are resistant to dissolution in the acidic environment of the stomach. Dosage forms coated with such polymers protect the drug from inactivation or degradation in the acidic environment or prevent irritation of the stomach by the drug.

It has been suggested to use HPMCAP to form solid amorphous dispersions with low-solubility drugs. A large number of presently known drugs have a low solubility in water, and thus complex techniques are required to prepare a dosage form. One known method includes dissolving such drug together with a pharmaceutically acceptable polymer, such as HPMCAP, in an organic solvent and to spray-dry the solution. The HPMCAP is aimed at reducing the crystallinity of the drug, thereby minimizing the activation energy necessary for the dissolution of the drug, as well as establishing hydrophilic conditions around the drug molecules, thereby improving the solubility of the drug itself to increase its bioavailability, i.e., its in vivo absorption by an individual upon ingestion.

International patent application WO 2006/082518 discloses hydroxypropyl methyl cellulose alkanyl phthalate polymers having a degree of substitution of phthalyl groups of at least 0.05, preferably at least 0.10, and a degree of substitution of alkanyl groups of at least 0.3, preferably of at least 0.4. HPMCAP polymers are exemplified that have a degree of substitution of phthalyl groups of 0.09-0.20 and a degree of substitution of acetyl groups of 0.61-0.90. The HPMCAP and a drug are dissolved in methanol or acetone and spray-dried to produce a spray-dried solid dispersion of the drug in the HPMCAP. However, organic solvents are often not desirable for pharmaceutical or nutritional uses. Moreover, the handling of organic solvents adds complexity.

H. Kokubo et al. disclose "Development of Cellulose Derivatives as Novel Enteric Coating Agents Soluble at pH 3.5-4.5 and Higher" in Chem. Pharm. Bull. 45(8) 1350-1353 (1997), Vol. 45, No. 8. Hydroxypropyl methyl cellulose (HPMC) was selected as base polymer to develop novel enteric coating agents for acid protection which can dissolve at pH around 4. HPMC was modified with trimellitic acid, phthalic acid, maleic acid or succinic acid at various degrees of substitution. The solubility in water of hydroxypropyl methyl cellulose trimellitate (HPMCT), hydroxypropyl methyl cellulose phthalate (HPMCP), hydroxypropyl methyl cellulose acetate maleate (HPMCAM) and hydroxypropyl methyl cellulose acetate succinate (HPMCAS) depending on their degree of neutralization was tested. As disclosed in the article of H. Kokubo et al., enteric coating polymers having carboxyl groups in their undissociated form have very low solubility in water. The degree of neutralization defines the ratio of deprotonated carboxylic groups over the sum of deprotonated and protonated carboxylic groups; i.e., the lower the degree of neutralization, the more carboxyl groups are present in their undissociated form. When the pH is raised by titration, the degree of neutralization of the carboxylic groups increases and water-solubility of the polymers increases. The solubility of the HPMC derivatives depends on the type of carboxylic groups and their degree of substitution, but all tested HPMC derivatives were insoluble in purified water when their degree of neutralization was less than 0.3. The solubility of HPMCP grade HP-50 was even insoluble in purified water when its degree of neutralization was up to 0.8. Unfortunately, coatings or capsules produced from such HPMC derivatives which have a sufficient degree of neutralization to be water-soluble are not sufficiently resistant to dissolution in the stomach and cannot protect the drug from inactivation or degradation in the acidic environment or prevent irritation of the stomach by the drug.

Accordingly, it would be desirable to find new types of esterified cellulose ethers which are water-soluble even at a low degree of neutralization. It would be even more desirable to find new types of esterified cellulose ethers which are water-soluble but still display resistance to dissolution in the acidic environment of the stomach.

Surprisingly, novel cellulose ether acetate phthalates have been found which can be dissolved in water although at least half of their phthalyl groups are non-neutralized. Moreover, the novel cellulose ether acetate phthalates display resistance to dissolution in the acidic environment of the stomach.

SUMMARY

One aspect of the present invention is a cellulose ether acetate phthalate wherein the degree of substitution of phthalyl groups is from 0.02 to 0.25, the degree of neutralization of phthalyl groups is not more than 0.5, the degree of substitution of acetyl groups is from 0.02 to 0.40, and the total degree of substitution of phthalyl and acetyl groups is not more than 0.50.

Another aspect of the present invention is a liquid composition which comprises at least one above-described cellulose ether acetate phthalate dissolved an aqueous diluent.

Yet another aspect of the present invention is a liquid composition which comprises at least one above-described cellulose ether acetate phthalate and an organic diluent.

Yet another aspect of the present invention is a process for coating a dosage form which comprises the step of contacting an above-mentioned liquid composition with the dosage form.

Yet another aspect of the present invention is a process for the manufacture of capsule shells which comprises the step of contacting the above-mentioned liquid composition with dipping pins.

Yet another aspect of the present invention is a coated dosage form wherein the coating comprises at least one above-described cellulose ether acetate phthalate.

Yet another aspect of the present invention is a polymeric capsule shell which comprises at least one above-described cellulose ether acetate phthalate.

Yet another aspect of the present invention is a capsule which comprises the above-mentioned capsule shell and further comprises a drug or a nutritional or food supplement or a combination thereof.

Yet another aspect of the present invention is a solid dispersion of at least one active ingredient in at least one above-described cellulose ether acetate phthalate.

DESCRIPTION OF EMBODIMENTS

Surprisingly, it has been found that the cellulose ether acetate phthalates of the present invention have a solubility in water of at least 2.0 weight percent at 2° C. Clear or turbid solutions with only a small portion of sediment or in the preferred embodiments even without sediment are obtained at a temperature of 2° C. or below. When the temperature of the prepared solution is increased to 15° C. or even to 20° C., no precipitation occurs. Moreover, aqueous solutions of the preferred embodiments of the cellulose ether acetate phthalate of the present invention gel at slightly elevated temperature. This renders the cellulose ether acetate phthalates of the present invention very useful in a variety of application, e.g. for producing capsules or for coating dosage forms. The advantages of the cellulose ether acetate phthalates of the present invention will be described in more detail below.

The cellulose ether acetate phthalate has a cellulose backbone having β-1,4 glycosidically bound D-glucopyranose repeating units, designated as anhydroglucose units in the context of this invention. The cellulose ether acetate phthalate preferably is an alkyl cellulose acetate phthalate, hydroxyalkyl cellulose acetate phthalate or hydroxyalkyl alkylcellulose acetate phthalate, more preferably a hydroxyalkyl methylcellulose acetate phthalate. This means that in the cellulose ether acetate phthalate of the present invention, at least a part of the hydroxyl groups of the anhydroglucose units are substituted by alkoxyl groups or hydroxyalkoxyl groups or a combination of alkoxyl and hydroxyalkoxyl groups. The hydroxyalkoxyl groups are typically hydroxymethoxyl, hydroxyethoxyl and/or hydroxypropoxyl groups. Hydroxyethoxyl and/or hydroxypropoxyl groups are preferred. Typically one or two kinds of hydroxyalkoxyl groups are present in the cellulose ether acetate phthalate. Preferably a single kind of hydroxyalkoxyl group, more preferably hydroxypropoxyl, is present. The alkoxyl groups are typically methoxyl, ethoxyl and/or propoxyl groups. Methoxyl groups are preferred. Illustrative of the above-defined cellulose ether acetate phthalates are alkylcellulose acetate phthalates, such as methylcellulose acetate phthalates and propylcellulose acetate phthalates; hydroxyalkylcellulose acetate phthalates, such as hydroxyethylcellulose acetate phthalates, hydroxypropylcellulose acetate phthalates, and hydroxybutylcellulose acetate phthalates; and hydroxyalkyl alkylcellulose acetate phthalates, such as hydroxyethyl methylcellulose acetate phthalates, hydroxymethyl ethylcellulose acetate phthalates, ethyl hydroxyethylcellulose acetate phthalates, hydroxypropyl methylcellulose acetate phthalates, hydroxypropyl ethylcellulose acetate phthalates, hydroxybutyl methylcellulose acetate phthalates, and hydroxybutyl ethylcellulose acetate phthalates; and those having two or more hydroxyalkyl groups, such as hydroxyethylhydroxypropyl methylcellulose acetate phthalates. Most preferably, the cellulose ether acetate phthalate is a hydroxyalkyl methylcellulose acetate phthalate, such as a hydroxypropyl methylcellulose acetate phthalate.

The degree of the substitution of hydroxyl groups of the anhydroglucose units by hydroxyalkoxyl groups is expressed by the molar substitution of hydroxyalkoxyl groups, the MS(hydroxyalkoxyl). The MS(hydroxyalkoxyl) is the average number of moles of hydroxyalkoxyl groups per anhydroglucose unit in the cellulose ether acetate phthalate. It is to be understood that during the hydroxyalkylation reaction the hydroxyl group of a hydroxyalkoxyl group bound to the cellulose backbone can be further etherified by an alkylation agent, e.g. a methylation agent, and/or a hydroxyalkylation agent. Multiple subsequent hydroxyalkylation etherification reactions with respect to the same carbon atom position of an anhydroglucose unit yields a side chain, wherein multiple hydroxyalkoxyl groups are covalently bound to each other by ether bonds, each side chain as a whole forming a hydroxyalkoxyl substituent to the cellulose backbone.

The term "hydroxyalkoxyl groups" thus has to be interpreted in the context of the MS(hydroxyalkoxyl) as referring to the hydroxyalkoxyl groups as the constituting units of hydroxyalkoxyl substituents, which either comprise a single hydroxyalkoxyl group or a side chain as outlined above, wherein two or more hydroxyalkoxy units are covalently bound to each other by ether bonding. Within this definition it is not important whether the terminal hydroxyl group of a hydroxyalkoxyl substituent is further alkylated, e.g. methylated, or not; both alkylated and non-alkylated hydroxyalkoxyl substituents are included for the determination of MS(hydroxyalkoxyl). The cellulose ether acetate phthalate of the invention generally has a molar substitution of hydroxyalkoxyl groups in the range 0.05 to 1.00, preferably 0.08 to 0.70, more preferably 0.15 to 0.60, most preferably 0.15 to 0.40, and particularly 0.20 to 0.40.

The average number of hydroxyl groups substituted by alkoxyl groups, such as methoxyl groups, per anhydroglucose unit, is designated as the degree of substitution of alkoxyl groups, DS(alkoxyl). In the above-given definition of DS, the term "hydroxyl groups substituted by alkoxyl groups" is to be construed within the present invention to include not only alkylated hydroxyl groups directly bound to the carbon atoms of the cellulose backbone, but also alkylated hydroxyl groups of hydroxyalkoxyl substituents bound to the cellulose backbone. The cellulose ether acetate phthalates according to this invention generally have a DS(alkoxyl) in the range of 1.0 to 2.5, preferably from 1.2 to 2.2, more preferably from 1.6 to 2.05, and most preferably from 1.7 to 2.05.

Most preferably the cellulose ether acetate phthalate is an hydroxypropyl methylcellulose acetate phthalate (HPMCAP) having a DS(methoxyl) within the ranges indicated above for DS(alkoxyl) and an MS(hydroxypropoxyl) within the ranges indicated above for MS(hydroxyalkoxyl).

An essential feature of the cellulose ether acetate phthalates of the present invention is their degree of substitution of phthalyl groups. The degree of substitution of phthalyl groups is at least 0.02, preferably at least 0.03, more preferably at least 0.04, and most preferably at least 0.05. The degree of substitution of phthalyl groups is not more than 0.25. In some embodiments of the invention the degree of substitution of phthalyl groups is up to 0.18 or up to 0.15 or even only up to 0.10. The cellulose ether acetate phthalates of the present invention have been found to gel at elevated temperatures as described in the Examples section, depending on their concentration in water.

The cellulose ether acetate phthalates of the present invention have a degree of substitution of acetyl groups, of from 0.02 to 0.40. The degree of substitution of acetyl groups preferably is at least 0.04, more preferably at least 0.05, and most preferably at least 0.07. In some embodiments of the invention degree of substitution of acetyl groups is at least 0.10. The cellulose ether acetate phthalates preferably have a degree of substitution of acetyl groups of up to 0.35, more preferably up to 0.30, and most preferably up to 0.25.

The total degree of substitution of phthalyl and acetyl groups is not more than 0.50, preferably not more than 0.45, more preferably not more than 0.40, and most preferably not more than 0.35. The total degree of substitution of phthalyl and acetyl groups preferably is at least 0.10, more preferably at least 0.15, and in some embodiments at least 0.20.

The content of the phthalyl groups in the cellulose ether acetate phthalates is determined as described for the phthalyl groups in Hypromellose phthalate, United States Pharmacopia and National Formulary, NF 33, pp. 6701-6702.

The content of the acetyl groups is determined in the same manner as described for "Hypromellose Acetate Succinate, United States Pharmacopia and National Formulary, NF 29, pp. 1548-1550".

The content of ether groups in the cellulose ether acetate phthalate is determined in the same manner as described for "Hypromellose", United States Pharmacopeia and National Formulary, USP 35, pp 3467-3469.

The contents of ether and ester groups obtained by the above analyses are converted to DS and MS values of individual substituents according to the formulas below. The formulas may be used in analogue manner to determine the DS and MS of substituents of other cellulose ether esters.

$$\% \text{ cellulose backbone} = 100 - \left(\% \text{ MeO} * \frac{M(OCH_3) - M(OH)}{M(OCH_3)}\right) -$$
$$\left(\% \text{ HPO} * \frac{M(OCH_2CH(OH)CH_3) - M(OH)}{M(OCH_2CH(OH)CH_3)}\right) -$$
$$\left(\% \text{ Acetyl} * \frac{M(COCH_3) - M(H)}{M(COCH_3)}\right) -$$
$$\left(\% \text{ Phthalyl} * \frac{M(COC_6H_4COOH) - M(H)}{M(COC_6H_4COOH)}\right)$$

$$DS(Me) = \frac{\frac{\% \text{ MeO}}{M(OCH_3)}}{\frac{\% \text{ cellulose backbone}}{M(AGU)}}$$

$$MS(HP) = \frac{\frac{\% \text{ HPO}}{M(HPO)}}{\frac{\% \text{ cellulose backbone}}{M(AGU)}}$$

$$DS(Phthalyl) = \frac{\frac{\% \text{ Phthalyl}}{M(Phthalyl)}}{\frac{\% \text{ cellulose backbone}}{M(AGU)}}$$

$$DS(Acetyl) = \frac{\frac{\% \text{ Acetyl}}{M(Acetyl)}}{\frac{\% \text{ cellulose backbone}}{M(AGU)}}$$

$M(MeO) = M(OCH_3) = 31.03 \; Da$ $M(HPO) = M(OCH_2CH(OH)CH_3) = 75.09 \; Da$ $M(Acetyl) = M(COCH_3) = 43.04 \; Da$ $M(Phthalyl) = M(COC_6H_4COOH) = 149.13 \; Da$ $M(AGU) = 162.14 \; Da$ $M(OH) = 17.008 \; Da$ $M(H) = 1.008 \; Da$ By convention, the weight percent is an average weight percentage based on the total weight of the cellulose repeat unit, including all substituents. The content of the methoxyl group is reported based on the mass of the methoxyl group (i.e., —$OCH_3$). The content of the hydroxyalkoxyl group is reported based on the mass of the hydroxyalkoxyl group (i.e., —O-alkylene-OH); such as hydroxypropoxyl (i.e., —O—$CH_2CH(CH_3)$—OH). The content of the acetyl group is reported based on the mass of the acetyl group (i.e., —C(O)—$CH_3$). The content of the phthalyl group is reported based on the mass of the phthalyl group (i.e., —C(O)—$C_6H_4$—COOH).

In the cellulose ether acetate phthalate of the present invention the degree of neutralization of the phthalyl groups is not more than 0.5, generally not more than 0.45, preferably not more than 0.4, more preferably not more than 0.3, most preferably not more than 0.1, and particularly not more than 0.05 or even not more than 0.01. The degree of neutralization can even be essentially zero or only slightly above it, e.g. up to $10^{-3}$ or even only up to $10^{-4}$. The term "degree of neutralization" as used herein defines the ratio of deprotonated carboxylic groups over the sum of deprotonated and protonated carboxylic groups, i.e., degree of neutralization=$[-C(O)-C_6H_4-COO^-]/[-C(O)-C_6H_4-COO^- + -C(O)-C_6H_4-COOH]$.

The degree of neutralization can be evaluated by titration as described by H. Kokubo et al. in "Development of Cellulose Derivatives as Novel Enteric Coating Agents Soluble at pH 3.5-4.5 and Higher" in *Chem. Pharm. Bull.* 45(8) 1350-1353 (1997), Vol. 45, No. 8, at page 1350. In neutralized phthalyl groups the counter-cations preferably are ammonium cations, such as $NH_4^+$, or alkali metal ions, such as sodium or potassium ions, more preferably sodium ions.

Surprisingly, it has been found that the cellulose ether acetate phthalate of the present invention has a solubility in water of at least 2.0 weight percent at 2° C., i.e., it can be dissolved as an at least 2.0 weight percent solution, preferably at least 3.0 weight percent solution, more preferably at least 5.0 weight percent solution, and most preferably even at least 10.0 weight percent solution in water at 2° C. Generally the cellulose ether acetate phthalate of the present invention can be dissolved as up to 20 weight percent solution or in the most preferred embodiments even as up to 30 weight percent solution in water at a temperature of 2° C. The term "an x weight percent solution in water at 2° C." as used herein means that x g of the cellulose ether acetate phthalate is soluble in (100–x) g of water at 2° C.

When determining the water solubility as described in the Examples section, the cellulose ether acetate phthalate of the present invention preferably has solubility properties that at least 85 wt. %, typically at least 90 wt. %, more typically at least 95 wt. %, and in many cases at least 99 wt. % of the cellulose ether acetate phthalate is soluble in a mixture of 2.5 weight parts of the cellulose ether acetate phthalate and 97.5 weight parts of water at 2° C. Typically this degree of solubility is also observed in a mixture of 5 or 10 weight parts of the cellulose ether acetate phthalate and 95 or 90 weight parts of water at 2° C. or even in a mixture of 20 weight parts of the cellulose ether acetate phthalate and 80 weight parts of water at 2° C.

In more general terms, it has surprisingly been found that the cellulose ether acetate phthalate of the present invention, in spite of its low degree of neutralization of phthalyl groups, is soluble in an aqueous liquid at a temperature of 2° C., even when the cellulose ether acetate phthalate is blended with an aqueous liquid that does not increase the degree of neutralization of the cellulose ether acetate phthalate to more than 0.5 or a preferred range listed above, e.g., when the cellulose ether acetate phthalate is blended with only water, such as deionized or distilled water. Clear or turbid solutions without sediment are obtained at 2° C.

Moreover, it has been found that aqueous solutions of a cellulose ether acetate phthalate of the present invention gel at elevated temperature, typically at 25 to 70° C., more typically at 30 to 60° C. This renders the cellulose ether acetate phthalate of the present invention very useful in a variety of application, e.g. for producing capsules and for coating dosage forms. Gelling of aqueous solutions of these cellulose ether acetate phthalates, such as hydroxypropyl methyl cellulose acetate phthalates (HPMCAP), at elevated temperature is observed even when aqueous solutions of the cellulose ethers that are used as starting materials for producing the cellulose ether acetate phthalates do not gel. E.g., the Examples of the present invention illustrate gelling HPMCAP of the present invention, although the corresponding hydroxypropyl methyl cellulose that is used as a starting material for preparing them does not gel to a significant degree. Gelation of the cellulose ether acetate phthalates of the present invention typically occurs at concentrations of 2 to 30 weight percent, more typically at 5 to 20 weight percent, based on the total weight of cellulose ether acetate phthalate and aqueous liquid. The gelation is reversible, i.e. upon cooling to 20° C. the gel transforms into a liquid aqueous solution.

The aqueous liquid in which the cellulose ether acetate phthalate of the present invention is soluble may additionally comprise a minor amount of an organic liquid diluent; however, the aqueous liquid should generally comprise at least 80, preferably at least 85, more preferably at least at least 90, and particularly at least 95 weight percent of water, based on the total weight of the aqueous liquid. The term "organic liquid diluent" as used herein means an organic solvent or a mixture of two or more organic solvents. Preferred organic liquid diluents are polar organic solvents having one or more heteroatoms, such as oxygen, nitrogen or halogen like chlorine. More preferred organic liquid diluents are alcohols, for example multifunctional alcohols, such as glycerol, or preferably monofunctional alcohols, such as methanol, ethanol, isopropanol or n-propanol; ethers, such as tetrahydrofuran; acetates, such as ethyl acetate; halogenated hydrocarbons, such as methylene chloride; or nitriles, such as acetonitrile. More preferably the organic liquid diluents have 1 to 6, most preferably 1 to 4 carbon atoms. The aqueous liquid may comprise a basic compound, but the degree of neutralization of the phthalyl groups of the cellulose ether acetate phthalate in the resulting blend of cellulose ether acetate phthalate and aqueous liquid should not be more than 0.50 or a preferred upper limit as described further above. Preferably the aqueous liquid does not comprise a substantial amount of a basic compound. More preferably, the aqueous diluent does not contain a basic compound. Even more preferably, the aqueous liquid comprises from 80 to 100 percent, preferably 85 to 100 percent, more preferably 90 to 100 percent and most preferably 95 to 100 percent of water, and from 0 to 20 percent, preferably 0 to 15 percent, more preferably 0 to 10 percent, and most preferably 0 to 5 percent of an organic liquid diluent, based on the total weight of the aqueous liquid. Most preferably the aqueous liquid consists of water, e.g., deionized or distilled water.

The cellulose ether acetate phthalate s of the present invention generally have a viscosity of up to 200 mPa·s, preferably up to 100 mPa·s, more preferably up to 50 mPa·s, and most preferably up to 5.0 mPa·s, measured as a 2.0 wt.-% solution of the cellulose ether acetate phthalate in 0.43 wt.-% aqueous NaOH at 20° C. Generally the viscosity is at least 1.2 mPa·s, more typically at least 1.8 mPa·s, even more typically at least 2.4 mPa·s, and most typically at least 2.8 mPa·s, measured as a 2.0 wt.-% solution of the cellulose ether acetate phthalate in 0.43 wt.-% aqueous NaOH at 20° C.

Details of the production of the cellulose ether acetate phthalates of the present invention are described in the examples. Some aspects of the production process are described below. The cellulose ether acetate phthalate of the present invention can be produced by esterifying a cellulose ether, such as an alkyl cellulose, hydroxyalkyl cellulose or hydroxyalkyl alkylcellulose described further above. The cellulose ether preferably has a DS(alkoxyl) and/or an MS(hydroxyalkoxyl) as described further above. The cellulose ether used as a starting material for esterification generally has a viscosity of from 1.2 to 200 mPa·s, preferably from 1.8 to 100 mPa·s, more preferably from 2.4 to 50 mPa·s and in particular from 2.8 to 5.0 mPa·s, measured as a 2 weight-% aqueous solution at 20° C. according to ASTM D2363-79 (Reapproved 2006). Cellulose ethers of such viscosity can be obtained by subjecting a cellulose ether of higher viscosity to a partial depolymerization process. Partial depolymerization processes are well known in the art and described, for example, in European Patent Applications EP 1,141,029; EP 210,917; EP 1,423,433; and U.S. Pat. No. 4,316,982. Alternatively, partial depolymerization can be achieved during the production of the cellulose ethers, for example by the presence of oxygen or an oxidizing agent.

The cellulose ether is reacted with phthalic anhydride and acetic anhydride. The molar ratio between the phthalic anhydride and the anhydroglucose units of the cellulose ether generally is at least 0.05:1, preferably at least 0.08:1, more preferably at least 0.10:1, and most preferably at least 0.12:1. The molar ratio between the phthalic anhydride and the anhydroglucose units of the cellulose ether generally is not more than 0.30:1, preferably not more than 0.25:1. The molar ratio between the acetic anhydride and the anhydroglucose units of the cellulose ether generally is at least 0.08:1, preferably at least 0.10:1, and more preferably at least 0.18:1. In the most preferred embodiments of the invention the molar ratio between the acetic anhydride and the anhydroglucose units of the cellulose ether is at least 0.25:1. The molar ratio between the acetic anhydride and the anhydroglucose units of the cellulose ether generally is up to 0.85:1, preferably up to 0.80:1, and more preferably up to 0.70:1. The total amount of the phthalic anhydride and acetic anhydride is chosen that a total degree of substitution of phthalyl and acetyl groups is not more than 0.50. When the molar ratio between the phthalic anhydride and the anhydroglucose units of the cellulose ether is at the upper end of the ranges disclosed above, typically the chosen molar ratio between the acetic anhydride and the anhydroglucose units of the cellulose ether is not at the upper end of the ranges disclosed above, and vice versa.

The molar number of anhydroglucose units of the cellulose ether utilized in the process can be determined from the weight of the cellulose ether used as a starting material, by calculating the average molecular weight of the substituted anhydroglucose units from the DS(alkoxyl) and MS(hydroxyalkoxyl).

The esterification of the cellulose ether is conducted in an aliphatic carboxylic acid as a reaction diluent, such as acetic acid, propionic acid, or butyric acid. The reaction diluent can comprise minor amounts of other solvents or diluents which are liquid at room temperature and do not react with the cellulose ether, such as aromatic or aliphatic solvents like benzene, toluene, 1,4-dioxane, or tetrahydrofurane; or halogenated $C_1$-$C_3$ derivatives, like dichloro methane or dichloro methyl ether, but the amount of the aliphatic carboxylic acid should generally be more than 50 percent, preferably at least 75 percent, and more preferably at least 90 percent, based on the total weight of the reaction diluent. Most preferably the reaction diluent consists of an aliphatic carboxylic acid, more preferably acetic acid. The molar ratio [aliphatic carboxylic acid/anhydroglucose units of cellulose ether] generally is from 9.5:1 to 11:1, preferably from 10.0:1 to 10.5:1.

The esterification reaction is conducted in the presence of an esterification catalyst, preferably in the presence of an alkali metal carboxylate, such as sodium acetate or potassium acetate. The molar ratio [alkali metal carboxylate/ anhydroglucose units of cellulose ether] is generally from [2.0/1.0] to [3.0/1.0], and preferably from [2.3/1.0] to [2.6/1.0].

The reaction temperature for the esterification is generally from 75° C. to 95° C., preferably from 80° C. to 90° C. The esterification reaction is typically completed within 2.5 to 4 hours. After completion of the esterification reaction, the cellulose ether acetate phthalate can be precipitated from the reaction mixture in a known manner, for example as described in U.S. Pat. No. 4,226,981, International Patent Application WO 2005/115330, European Patent Application EP 0 219 426 or International Patent Application WO2013/148154. The precipitated cellulose ether acetate phthalate is typically washed with an aqueous liquid at a temperature of from 70 to 100° C. Suitable aqueous liquids are described further above.

Another aspect of the present invention is an aqueous composition comprising one or more of the above described cellulose ether acetate phthalates of the present invention dissolved in an aqueous liquid. The aqueous liquid is a described further above. The cellulose ether acetate phthalate of the present invention can be brought into aqueous solution by cooling the aqueous composition to a temperature of −2° C. to less than 10° C., preferably of 0° C. to less than 8° C., more preferably of 0.5° C. to less than 5° C., and most preferably of 0.5° C. to 3° C. The aqueous composition preferably comprises at least 5 wt.-%, more preferably at least 10 wt.-%, and preferably up to 30 wt.-%, more preferably up to 20 wt.-% of the cellulose ether acetate phthalate of the present invention, based on the total weight of the aqueous composition.

The aqueous composition comprising one or more of the above described cellulose ether acetate phthalates of the present invention dissolved in an aqueous liquid is useful in the manufacture of capsules wherein the liquid composition is contacted with dipping pins. Typically an aqueous composition having a temperature of less than 20° C., more typically less than 15° C. or in some embodiments less than 10° C. is contacted with dipping pins having a higher temperature than the aqueous composition and that have a temperature of at least 21° C., more typically at least 25° C., and up to 95° C., preferably up to 80° C.

The aqueous composition comprising one or more of the above described cellulose ether acetate phthalates dissolved in an aqueous liquid is also useful for coating dosage forms, such as tablets, granules, pellets, caplets, lozenges, suppositories, pessaries or implantable dosage forms.

Another aspect of the present invention is a liquid composition comprising an organic diluent and one or more of the above described cellulose ether acetate phthalates of the present invention. The organic diluent may be present in the liquid composition alone or mixed with water. Preferred organic diluents are described further above. The liquid composition preferably comprises at least 5 wt.-%, more preferably at least 10 wt.-%, and preferably up to 30 wt.-%, more preferably up to 20 wt.-% of the cellulose ether acetate phthalate of the present invention, based on the total weight of the liquid composition.

The composition of the present invention comprising an aqueous liquid or an organic diluent as described above and one or more of the above described cellulose ether acetate phthalates is also useful as an excipient system for active ingredients and particularly useful as an intermediate for preparing an excipient system for active ingredients, such as fertilizers, herbicides or pesticides, or biologically active ingredients, such as vitamins, herbals and mineral supplements or drugs. Accordingly, the composition of the present invention preferably comprises one or more active ingredients, most preferably one or more drugs. The term "drug" is conventional, denoting a compound having beneficial prophylactic and/or therapeutic properties when administered to an animal, especially humans. In another aspect of the invention the composition of the present invention is used for producing a solid dispersion comprising at least one active ingredient, such as a drug, at least one cellulose ether acetate phthalate as described above and optionally one or more adjuvants. A preferred method of producing a solid dispersion is by spray-drying. Spray-drying processes and spray-drying equipment are described generally in Perry's Chemical Engineers' Handbook, pages 20-54 to 20-57 (Sixth Edition 1984). Alternatively, the solid dispersion of the present invention may be prepared by i) blending a) at least one cellulose ether acetate phthalate defined above, b) one or more active ingredients and c) one or more optional additives, and ii) subjecting the blend to extrusion. The term "extrusion" as used herein includes processes known as injection molding, melt casting and compression molding. Techniques for extruding, preferably melt-extruding compositions comprising an active ingredient such as a drug is known and described by Joerg Breitenbach, Melt extrusion: from process to drug delivery technology, European Journal of Pharmaceutics and Biopharmaceutics 54 (2002) 107-117 or in European Patent Application EP 0 872 233. The solid dispersion of the present invention preferably comprises a) from 20 to 99.9 percent, more preferably from 30 to 98 percent, and most preferably from 60 to 95 percent of an cellulose ether acetate phthalate as described above, and b) preferably from 0.1 to 80 percent, more preferably from 2 to 70 percent, and most preferably from 5 to 40 percent of an active ingredient b), based on the total weight of the cellulose ether acetate phthalate a) and the active ingredient b). The combined amount of the cellulose ether acetate phthalate a) and the active ingredient b) is preferably at least 70 percent, more preferably at least 80 percent, and most preferably at least 90 percent, based on the total weight of the solid dispersion. The remaining amount, if any, consists of one or more of the adjuvants c) as described below. Once the solid dispersion comprising at least one active ingredient in at least one cellulose ether acetate phthalate has been formed, several processing operations can be used, such as drying, granulation, and milling, to facilitate incorporation of the dispersion into a dosage form, such as strands, pellets, granules, pills, tablets, caplets, microparticles, fillings of capsules or injection molded capsules or in the form of a powder, film, paste, cream, suspension or slurry.

The aqueous composition, the liquid composition comprising an organic diluent and the solid dispersion of the present invention may further comprise optional adjuvants, such as coloring agents, pigments, opacifiers, flavor and taste improvers, antioxidants, and any combination thereof.

Some embodiments of the invention will now be described in detail in the following Examples.

EXAMPLES

Unless otherwise mentioned, all parts and percentages are by weight. In the Examples the following test procedures are used.

Content of Ether and Ester Groups

The content of ether groups in the cellulose ether acetate phthalate is determined in the same manner as described for "Hypromellose", United States Pharmacopeia and National Formulary, USP 35, pp 3467-3469.

The content of the phthalyl groups is determined according to Hypromellose phthalate, United States Pharmacopia and National Formulary, NF 33, pp. 6701-6702.

The content of the acetyl groups is determined in the same manner as described for "Hypromellose Acetate Succinate, United States Pharmacopia and National Formulary, NF 29, pp. 1548-1550".

Water-Solubility of Hydroxypropyl Methyl Cellulose Acetate Phthalate (HPMCAP)

Quantitative Determination: 2.5 weight parts of HPMCAP, based on its dry weight, were added to 97.5 weight parts of deionized water having a temperature of 2° C. followed by stirring for 6 hours at 2° C. and storing for 16 h at 2° C. A weighed amount of this mixture was transferred to a weighed centrifuge vial; the transferred weight of the mixture was noted as M1 in g. The transferred weight of HPMCAP [M2] was calculated as (transferred weight of mixture in g/100 g×2.5 g). The mixture was centrifuged for 60 min at 5000 rpm (2823×g, Biofuge Stratos centrifuge from Thermo Scientific) at 2° C. After centrifugation an aliquot was removed from the liquid phase and transferred to a dried weighed vial. The weight of the transferred aliquot was recorded as M3 in g. The aliquot was dried at 105° C. for 12 h. The remaining g of HPMCAP was weighed after drying and recorded as M4 in g.

The term "% water soluble at 2.5%" in Table 2 below expresses the percentage of HPMCAP that is actually dissolved in the mixture of 2.5 weight parts of HPMCAP and 97.5 weight parts of deionized water. It is calculated as (M4/M2)×(M1/M3)×100, which corresponds to (g HPMCAP in liquid aliquot/g HPMCAP transferred to centrifuge vial)×(g mixture transferred to centrifuge vial/g liquid aliquot after centrifugation)×100. In the formulas above "×" stands for the multiplication operator.

Qualitative Determination: A 2 wt. percent mixture of HPMCAP and water was prepared by mixing 2.0 g HPMCAP, based on its dry weight, with 98.0 g water under vigorous stirring at 0.5° C. for 16 hours. The temperature of the mixture of HPMCAP and water was then increased to 4° C. in a refrigerator. HPMCAP that is soluble at 4° C. is also soluble at 2° C.; at 2° C. the solubility is at least as high as at 4° C. The water solubility of the HPMCAP was determined by visual inspection. The determination whether the HPMCAP was water-soluble at 2% at 2° C. or not was done as follows. "Water soluble at 2%—yes" means that a solution without sediment was obtained according to the procedure above. "Water soluble at 2%—no" means that at least a significant portion of the HPMCAP remained undissolved and formed sediment when mixing 2.0 g HPMCAP, based on its dry weight, with 98.0 g water according to the procedure above.

Viscosity of Hydroxypropyl Methyl Cellulose Acetate Phthalate (HPMCAP)

A 2.0% by weight solution of the HPMCAP in 0.43 wt. % aqueous NaOH was prepared as described in "Hypromellose Phthalate, United States Pharmacopia and National Formulary, NF. An Ubbelohde viscosity measurement according to DIN 51562-1:1999-01 (January 1999) was carried out. The measurement was done at 20° C. The 2.0% by weight solution of the HPMCAP in 0.43 wt. % aqueous NaOH is listed in Table 2 below as "2.0% viscosity in 0.43% NaOH".

The 10 wt.-% solution of HPMCAP in a 1:1 by weight mixture of dichloromethane and methanol was prepared by mixing 10.0 g HPMCAP with 45.0 g of dichloromethane and 45.0 g of methanol under vigorous stirring at room temperature. The mixture was rolled on a roller mixer for about 24 hours. The solution was centrifuged at 2000 rpm for 3 minutes using a Megafuge 1.0 centrifuge, commercially available from Heraeus Holding GmbH, Germany. An Ubbelohde viscosity measurement according to DIN 51562-1:1999-01 (January 1999) was carried out. The measurement was done at 20° C.

Gelation Temperature and Gel Strength of Solutions of HPMCAP in Water

A 2 wt.-%, 5 wt.-% or 10 wt.-% solution of HPMCAP in water was produced by adding a corresponding amount of milled, ground, and dried HPMCAP (under consideration of the water content of the HPMCAP) to water (temperature 20-25° C.) at room temperature while stirring with an overhead lab stirrer at 750 rpm with a 3-wing (wing=2 cm) blade stirrer. The solution was then cooled to about 1.5° C. After the temperature of 1.5° C. was reached the solution was stirred for 120 min at 500 rpms. Each solution was stored in the refrigerator prior to the characterization.

Rheology measurements of the HPMCAP solutions in water were conducted with a Haake RS600 (Thermo Fisher Scientific) rheometer with cup and bob fixtures (CC-25). The samples were heated at a rate of 1° C. per minute over a temperature range from 5 to 85° C. with a constant strain (deformation) of 2% and a constant angular frequency of 2 Hz. The measurement collection rate was chosen to be 4 data points/min. The storage modulus G', which was obtained from the rheology measurements, represents the elastic properties of the solution and represents the gel strength in the high temperature region, when the storage modulus G' is higher than the loss modulus G".

The obtained data of the storage modulus G', which was obtained from the oscillation measurements, was first logarithmized and normalized to G' (min) to zero and G' (max) to 100. Linear regression curves were fitted to subsets of these storage modulus data (increments of 5 data points). A tangent was fitted to the steepest slope of the regression curve. The intersection of this tangent with the x-axis is reported as gelation temperature. Details how to determine the gelation temperature are described in International Patent Application WO2015/009796 on pages 18 and 19 in the paragraphs "Determination of the gelation temperature of aqueous compositions comprising methyl cellulose".

The gel strength according to the storage modulus G' at 65° C. was also obtained by this rheology measurement.

Production of HPMCAP of Examples 1-8 and Comparative Examples A-F 700.0 g of acetic acid was filled in a reactor and stirred. Then 230.0 g of sodium acetate (water free) and 230.0 g of HPMC (water free) were added. The HPMC had a methoxyl substitution $(DS_M)$ of 1.98, a hydroxypropoxyl substitution $(MS_{HP})$ of 0.25 and a viscosity of 3.0 mPa·s, measured as a 2% solution in water at 20° C. according to ASTM D2363-79 (Reapproved 2006). The weight average molecular weight of the HPMC was about 20,000 Dalton. The HPMC is commercially available from The Dow Chemical Company as Methocel E3 LV Premium cellulose ether. Inertisation with nitrogen was carried out. The mixture was heated to 85° C. under stirring. After reaching the temperature of 85° C. the reaction mixture was allowed to stir for 10 min. Then phthalic anhydride and acetic anhydride as listed in Table 1 below were added, and the reaction mixture was allowed to react for 3.5 hours. After the esterification reaction the mixture was quenched with 318 g of deionized water having a temperature of 50° C. Then 2 L, of deionized water (temperature 50° C.) was added into the reactor under stirring to precipitate the HPMCAP. The precipitated HPMCAP cooled down to about 50° C. and was removed from the reactor. The HPMCAP was washed several times with 1.7 L of hot water (temperature about 95° C.) by applying high shear mixing using an Ultra-Turrax stirrer S50-G45 running at 5000 rpm for 60 seconds. After filtration the filter cake was washed several times with 1.7 L of hot water. The washed HPMCAP was isolated by vacuum-filtration and dried at 55° C. overnight.

TABLE 1

| (Comparative) Example | HPMC g | HPMC Mol | Glacial acetic acid g | Glacial acetic acid mol/mol HPMC | Phthalic anhydride g | Phthalic anhydride mol/mol HPMC | Acetic anhydride g | Acetic anhydride mol/mol HPMC | Sodium acetate g | Sodium acetate mol/mol HPMC |
|---|---|---|---|---|---|---|---|---|---|---|
| 1 | 230 | 1.14 | 700 | 10.3 | 20.0 | 0.12 | 10.0 | 0.09 | 230 | 2.46 |
| 2 | 230 | 1.14 | 700 | 10.3 | 20.0 | 0.12 | 20.0 | 0.18 | 230 | 2.46 |
| 3 | 230 | 1.14 | 700 | 10.3 | 20.0 | 0.12 | 30.0 | 0.27 | 230 | 2.46 |
| 4 | 230 | 1.14 | 700 | 10.3 | 20.0 | 0.12 | 40.0 | 0.36 | 230 | 2.46 |
| 5 | 230 | 1.14 | 700 | 10.3 | 20.0 | 0.12 | 50.0 | 0.45 | 230 | 2.46 |
| 6 | 230 | 1.14 | 700 | 10.3 | 20.0 | 0.12 | 60.0 | 0.54 | 230 | 2.46 |
| 7 | 230 | 1.14 | 700 | 10.3 | 20.0 | 0.12 | 70.0 | 0.64 | 230 | 2.46 |
| 8 | 230 | 1.14 | 700 | 10.3 | 40.0 | 0.24 | 10.0 | 0.09 | 230 | 2.46 |
| A | 230 | 1.14 | 700 | 10.3 | 20.0 | 0.12 | 100 | 0.89 | 5 | 2.46 |
| B | 230 | 1.14 | 700 | 10.3 | 20.0 | 0.12 | 150 | 1.33 | 230 | 2.46 |
| C | 230 | 1.14 | 700 | 10.3 | 80.0 | 0.48 | 50.0 | 0.45 | 230 | 2.46 |
| D | 230 | 1.14 | 700 | 10.3 | 100 | 0.60 | 50.0 | 0.45 | 230 | 2.46 |
| E | 230 | 1.14 | 700 | 10.3 | 150 | 0.90 | 50.0 | 0.45 | 230 | 2.46 |
| F | 230 | 1.14 | 700 | 10.3 | 100 | 0.60 | 100 | 0.89 | 230 | 2.46 |

The properties of the HPMCAP of Examples 1-8 and Comparative Examples A-F are listed in Table 2 below. In Table 2 the abbreviations have the following meanings:

$DS_M$=DS(methoxyl): degree of substitution of methoxyl groups;

$MS_{HP}$=MS(hydroxypropoxyl): molar substitution of hydroxypropoxyl groups;

$DS_{ac}$=degree of substitution of acetyl groups;

$DS_{Ph}$: degree of substitution of phthalyl groups.

The results in Table 2 below illustrate that the cellulose ether acetate phthalates of Examples 1-8 are soluble in water, but those of Comparative Examples A-F are not or insufficiently soluble in water. Moreover, cellulose ether acetate phthalates of Examples 1-8 are soluble in some polar solvents, such as a mixture of dicloromethane and methanol. Even at 10 wt.-% solution the viscosity is low, similar to that of Comparative Example A.

Warming Up of Aqueous Solutions of HPMCAP

Aqueous solutions of 2 wt. % HPMCAP were prepared as described above in the paragraph "Water-Solubility", Qualitative determination". Subsequently the mixtures were gradually warmed up by storing them at 40° C. for 1 hour, then at 50° C. for 1 hour, then at 60° C. for 1 hour, then at 70° C. for 1 hour, and then at 80° C. for 1 hour. The effect of the temperature increase on the solutions was visually inspected. The results are listed in Table 3 below.

Only the warming up of the aqueous solutions of Examples 1-8 was assessed. Comparative Examples were not assessed because of insufficient water solubility and the formation of sediment.

TABLE 2

| (Comp.) Example | Methoxyl (%) | Hydroxypropoxyl (%) | Acetyl (%) | Phthalyl (%) | $DS_{ac}$ | $DS_{Ph}$ | % water soluble at 2.5% (quantitative) | Water-soluble at 2% (qualitative) | 2% viscosity in 0.43% NaOH [mPa · s] | Viscosity 10 wt.-% sol. in organic solvent (mPa · s) |
|---|---|---|---|---|---|---|---|---|---|---|
| 1 | 27.9 | 8.6 | 0.8 | 3.7 | 0.04 | 0.05 | 98 | Yes[1] | 4.1 | 76* |
| 2 | 28.6 | 8.8 | 1.3 | 4.1 | 0.07 | 0.06 | 100 | Yes[1] | 3.9 | 74* |
| 3 | 28.3 | 8.8 | 1.7 | 4.6 | 0.09 | 0.07 | 99 | Yes[1] | 3.8 | 82* |
| 4 | 28.0 | 8.3 | 2.4 | 5.2 | 0.12 | 0.08 | 99 | Yes[1] | 3.7 | 114* |
| 5 | 27.5 | 8.2 | 3.0 | 5.7 | 0.16 | 0.09 | 99 | Yes[1] | 3.6 | 176* |
| 6 | 27.1 | 8.1 | 3.8 | 6.2 | 0.20 | 0.09 | 98 | Yes[2] | 3.4 | 152* |
| 7 | 26.7 | 8.0 | 4.5 | 6.6 | 0.22 | 0.10 | 83 | Yes[2] | 3.3 | 139* |
| 8 | 28 | 8.4 | 0.7 | 7.1 | 0.04 | 0.11 | 97 | Yes[1] | 3.8 | 63* |
| A | 25.3 | 7.5 | 8.8 | 6.0 | 0.49 | 0.10 | 56 | No[3] | 3.0 | 105** |
| B | 24.8 | 7.4 | 11.6 | 5.3 | 0.66 | 0.09 | 56 | No[3] | 2.9 | 17.1** |
| C | 22.9 | 6.8 | 2.2 | 21.2 | 0.14 | 0.38 | 3 | No[3] | 2.9 | 20.3** |
| D | 22.1 | 6.6 | 1.9 | 24.4 | 0.12 | 0.45 | 2 | No[3] | 2.9 | 11.7** |
| E | 20.5 | 6.1 | 1.5 | 29.7 | 0.10 | 0.59 | 2 | No[3] | 2.8 | 8.9** |
| F | 22.0 | 6.5 | 6.1 | 20.1 | 0.39 | 0.37 | 3 | No[3] | 2.8 | 8.8** |

[1] clear solution
[2] slightly turbid
[3] sediment formed
*organic solvent is 1:1 dichloromethane/methanol
**organic solvent is acetone

TABLE 3

| (Comp.) Example | After 1 hour at 40° C. | After 1 hour at 50° C. | After 1 hour at 60° C. | After 1 hour at 70° C. | After 1 hour at 80° C. |
|---|---|---|---|---|---|
| 1 | Clear solution | Milky, very slightly gelling | Milky white, coagulates, flows | Milky white, coagulates, syneresis | Plug formed that falls easily apart; in liquid |

TABLE 3-continued

| (Comp.) Example | After 1 hour at 40° C. | After 1 hour at 50° C. | After 1 hour at 60° C. | After 1 hour at 70° C. | After 1 hour at 80° C. |
|---|---|---|---|---|---|
| 2 | Slightly milky solution | Milky, very soft gel, flows | Milky, soft gel, flows | Milky, soft gel, flows; syneresis | Plug formed that falls easily apart, in liquid |
| 3 | Slightly milky solution | Milky, very soft gel, does not flow | milky, soft gel; does not flow | milky, soft gel; does not flow, syneresis | Plug formed, in aqueous liquid |
| 4 | Slightly milky solution | milky, turbid; forms gel; gel does not flow when vial turned upside down | milky, turbid; forms gel; gel does not flow when vial turned upside down | Shrunk, white, moderately hard plug in aqueous liquid | Shrunk, white, relatively hard plug in separated liquid |
| 5 | Slightly milky, turbid; slightly gelling, flows well | milky, turbid; forms soft gel; gel does not flow when vial turned upside down | milky, turbid; forms soft gel; does not flow when vial turned upside down | Shrunk, white, moderately hard plug in aqueous liquid | Shrunk, white, relatively hard plug in separated liquid |
| 6 | milky, turbid; soft gel | milky, turbid; soft gel; gel does not flow when vial turned upside down | Milky white, soft plug; syneresis | Shrunk, white, moderately hard plug in aqueous liquid | Shrunk, white, quite hard plug in separated liquid |
| 7 | milky, turbid; hardly gelling; flows well | milky, turbid, forms flakes, syneresis | Soft, white plug in aqueous liquid | Shrunk, white, not very hard plug in liquid | Shrunk, white, relatively hard plug |
| 8 | Milky solution | Milky, white, watery | Milky, white, very large flakes | Milky, white, very large flakes | Large, white flakes that agglomerate to a plug |

Gelation

Aqueous solutions of the HPMCAP of the present invention gel at elevated temperature, typically at 25 to 70° C., more typically at 30 to 60° C. Aqueous solutions of the HPMCAP of the present invention even gel at a concentration as low as 2 wt.-%. It is very surprising that the cellulose ether acetate phthalates gel in spite of their low degree of ester substitution. The HPMC that is used as starting material for preparing the HPMCAP does not gel at a concentration of 2 wt.-%. A 2 wt.-% solution of Methocel E3 LV Premium cellulose ether in water after heating to 65° C. does not form a gel but only flocculates.

Rheology measurements were carried out to measure the gelation temperatures and gel strength according to the storage modulus G' at 65° C. of 2 wt.-%, 5 wt.-% and/or 10 wt.-% solutions of the HPMCAP of Examples 1, 2, 4 and 5 in water as described further above. The results are listed in Table 4 below.

TABLE 4

| Example | Wt.-% HPMCAP in water | Gelation Temperature, ° C. | Gel Strength G' at 65° C., Pa |
|---|---|---|---|
| 1 | 2 | 51 | 39 |
| 1 | 5 | 47 | 1014 |
| 1 | 10 | 45 | 4685 |
| 2 | 2 | 49 | 76 |
| 2 | 5 | 44 | 1633 |
| 4 | 2 | 43 | 173 |
| 4 | 5 | 37 | 3236 |
| 4 | 10 | 32 | 10340 |
| 5 | 2 | 42 | 191 |
| 5 | 5 | 34 | 3921 |
| 5 | 10 | 29 | 16990 |
| Methocel E3 LV Premium cellulose ether | 2 | 55 | 0.6 * |
| Methocel E3 LV Premium cellulose ether | 5 | 63 | 2 |
| Methocel E3 LV Premium cellulose ether | 10 | 58 | 73 |

* No significant gelling, only flocculation

Enteric Properties of the HPMCAP

To test the solubility of the HPMCAP in the stomach, HPMCAP in powder form at a concentration of 1 wt. % was stirred in 0.1 N HCl for 2 hours at a temperature of 37° C. to simulate the stomach fluid.

To test the solubility of the HPMCAP in the intestine or colon, HPMCAP in powder form at a concentration of 1 wt. % was stirred in McIlvaine's buffer solutions (containing disodium monophosphate and citric acid) that had a temperature of 37° C. and a pH of 3.0; 4.0; 4.5; 5.0; 5.5; 6.0 or 6.8, respectively.

The results are listed in Table 5 below.

TABLE 5

| | 0.1M HCl | | McIlvaine's buffer | | | | | |
|---|---|---|---|---|---|---|---|---|
| Example | liquid | HPMCAP | pH 6.8 | pH 6.0 | pH 5.5 | pH 5.0 | pH 4.0 | pH 3.0 |
| 1 | st | ○ | — | — | — | — | — | x |
| 2 | st | x | — | — | — | — | x | x |
| 3 | t | x | — | — | — | ○ | x | x |
| 4 | c | x | ○ | — | — | slightly ○ | x | x |
| 5 | c | x | ○ | — | — | slightly ○ | x | x |
| 6 | c | x | ○ | ○ | ○ | slightly ○ | x | x |
| 7 | c | x | ○ | ○ | ○ | x | x | x |

TABLE 5-continued

| | 0.1M HCl | | McIlvaine's buffer | | | | | |
|---|---|---|---|---|---|---|---|---|
| Example | liquid | HPMCAP | pH 6.8 | pH 6.0 | pH 5.5 | pH 5.0 | pH 4.0 | pH 3.0 |
| 8 | t | x | — | — | o | slightly o | x | x | st: slightly turbid
t: turbid
c: clear
o: swollen
x: insoluble
—: dissolved

The results in Table 5 above illustrate that the cellulose ether acetate phthalates of the present invention are not only water-soluble (see Table 2 above) but that they also display enteric properties, i.e., they display resistance to dissolution in the acidic environment of the stomach but are soluble in the intestine or colon.

The invention claimed is:

1. A hydroxypropyl methyl cellulose acetate phthalate wherein
   the degree of substitution of phthalyl groups is from 0.02 to 0.25, the degree of neutralization of phthalyl groups is not more than 0.5, wherein the degree of neutralization=[—C(O)—C$_6$H$_4$—COO$^-$]/[—C(O)—C$_6$H$_4$—COO$^-$+—C(O)—C$_6$H$_4$—COOH], and
   the degree of substitution of acetyl groups is from 0.07 to 0.25.

2. The hydroxypropyl methyl cellulose acetate phthalate of claim 1 having a solubility in water of at least 2.0 weight percent at 2° C.

3. The hydroxypropyl methyl cellulose acetate phthalate of claim 1 wherein the degree of substitution of phthalyl groups is from 0.04 to 0.15.

4. The hydroxypropyl methyl cellulose acetate phthalate of claim 1 wherein at least 85 wt. % of the hydroxypropyl methyl cellulose acetate phthalate is soluble in a mixture of 2.5 weight parts of the hydroxypropyl methyl cellulose acetate phthalate and 97.5 weight parts of water at 2° C.

5. A liquid composition comprising at least one hydroxypropyl methyl cellulose acetate phthalate of claim 1 dissolved in an aqueous liquid.

6. The liquid composition of claim 5 having a temperature of less than 15° C.

7. A liquid composition comprising at least one hydroxypropyl methyl cellulose acetate phthalate of claim 1 and an organic diluent.

8. A process for coating a dosage form comprising the step of contacting the liquid composition of claim 5 with the dosage form.

9. A process for the manufacture of capsule shells comprising the step of contacting the liquid composition of claim 5 with dipping pins.

10. A coated dosage form wherein the coating comprises at least one hydroxypropyl methyl cellulose acetate phthalate of claim 1.

11. A polymeric capsule shell comprising at least one hydroxypropyl methyl cellulose acetate phthalate of claim 1.

12. A capsule comprising a capsule shell of claim 11 and further comprising a drug or a nutritional or food supplement or a combination thereof.

13. A solid dispersion of at least one active ingredient in at least one hydroxypropyl methyl cellulose acetate phthalate of claim 1.

14. A process for coating a dosage form comprising the step of contacting the liquid composition of claim 7 with the dosage form.

15. A process for the manufacture of capsule shells comprising the step of contacting the liquid composition of claim 7 with dipping pins.

* * * * *